United States Patent
Mignani et al.

Patent Number: 5,359,072
Date of Patent: Oct. 25, 1994

[54] NONLINEARLY OPTICALLY ACTIVE COMPOUNDS

[75] Inventors: Gerard Mignani, Lyons; Gerard Soula, Meyzieu; Remi Meyrueix, Lyons, all of France

[73] Assignee: Rhone-Poulenc Chimie, Courbevoie, France

[21] Appl. No.: 714,585

[22] Filed: Jun. 13, 1991

Related U.S. Application Data

[63] Continuation of Ser. No. 407,744, Sep. 15, 1989, abandoned.

[30] Foreign Application Priority Data

Sep. 15, 1988 [FR] France .................. 88 12028

[51] Int. Cl.$^5$ .................. C07D 451/02; G02F 1/35
[52] U.S. Cl. .................. 546/94; 558/426; 548/566; 549/35
[58] Field of Search .................. 546/94; 558/426

[56] References Cited

FOREIGN PATENT DOCUMENTS 2345189 1/1974 Fed. Rep. of Germany ...... 558/430
3214724 9/1988 Japan .................. 548/570

OTHER PUBLICATIONS

Tripathy, et al. Chem. Tech. 1989 pp. 747–752.
Lemke Chem. Ber. 103 1894–1899 (1970).
Lemke, Chem. Ber. 103 3003–3006, 1970.
Smith, Optics (New York, J. Wiley and Sons, 1988) p. 266.
Approaches for Optimizing the First Electronic Hyperpolarizability of Conjugated Organic Molecules, S. R. Marder et al., Science, vol. 252, Apr. 5, 1991.
Experimental Investigations of Organic Molecular Nonlinear Optical Polarizabilities. Methods and Results on Benzene and Stilbene Derivatives, Lap-Tak Cheng, et al., J. Phys. Chem., vol. 95, No. 26, American Chemical Society, 1991.
Second Harmonic Generation in Poled Polymer Films, K. D. Singer et al., Appl. Phys. Lett. 49(5), vol. 49, No. 5, Aug. 4, 1986.
Second-order Nonlinear-optical Processes in Orientationally Ordered Materials: Relationship Between Molecular and Macroscopic Properties, K. D. Singer et al., Optical Society of America, vol. 4, No. 6, Jun. 1987.

Primary Examiner—Robert T. Bond
Assistant Examiner—P. K. Sripada
Attorney, Agent, or Firm—Burns, Doane, Swecker & Mathis

[57] ABSTRACT

Novel nonlinearly optically active compounds, well suited for electrooptical applications, have the following general formulae:

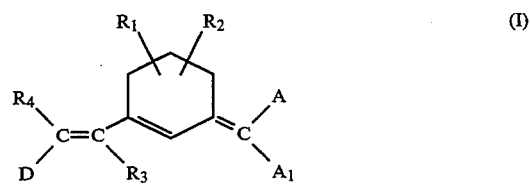

and

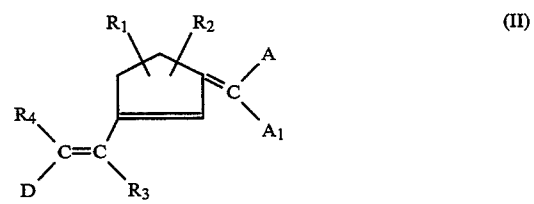

wherein D is an electron donor group; A and $A_1$, which may be identical or different, are each an electron acceptor group; and $R_1$, $R_2$, $R_3$ and $R_4$ are each a lower alkyl radical or a hydrogen atom.

11 Claims, No Drawings

NONLINEARLY OPTICALLY ACTIVE COMPOUNDS

This application is a continuation of application Ser. No. 07/407,744, filed Sep. 15, 1989 now abandoned.

BACKGROUND OF THE INVENTION

1. Field of the Invention

The present invention relates to novel organic compounds having nonlinear optical activity, and, more especially, to novel hyperpolarizable organic compounds well suited for inclusion in a matrix material to constitute a component of an electrooptical device.

2. Description of the Prior Art

As indicated by J. Zyszs and I. Ledoux, in an article published in *L'Echo des Recherches*, 1st trimester 1987, under the title "Organic Molecules and Treatment of Optical Signals", the future of optical telecommunications mandates the availability of components fabricated from materials having a strong nonlinear activity, on the second or third order.

Numerous compounds, both organic and inorganic, are used in different forms, such as solutions, liquid crystals, single-crystals, liquid polymer crystals, and the like.

Organic compounds are of great interest, as syntheses of a very wide variety of products, are typically enabled thereby. Furthermore, most organic compounds are highly resistant to deleterious external influences (humidity, acidity, oxidation, etc.) and may be incorporated in such materials as polymer films or the like.

J. F. Nicoud and R. J. Twieg, in their paper entitled "Design and Synthesis of Organic Molecular Compounds for Efficient Second Harmonic Generation", Ed. D. S. Chemla and J. Zyss (1987), report several molecules capable of nonlinear optical activity.

These molecules have carbon chain skeletons typically containing aromatic rings substituted, on the one hand, by electron donating groups and, on the other, by electron accepting groups.

The dislocation of electrons generates strong hyperpolarizabilities on the third and second order, when the molecule is noncentrosymmetric.

Large scale research efforts are continuously underway to discover and synthesize novel compounds having a nonlinear optical activity.

SUMMARY OF THE INVENTION

Accordingly, a major object of the present invention is the provision of a novel class of organic compounds having high nonlinear optical activity.

Briefly, the present invention features novel hyperpolarizable organic compounds having nonlinear optical activity and conforming to the following formulae:

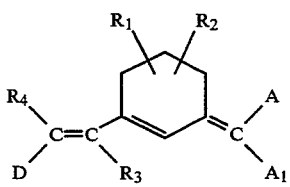

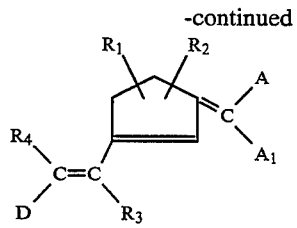

in which D is an electron donor group; A and $A_1$, which may be identical or different, are each an electron acceptor group; and $R_1$, $R_2$, $R_3$ and $R_4$ are each lower alkyl radicals or a hydrogen atom.

DETAILED DESCRIPTION OF THE PREFERRED EMBODIMENTS OF THE INVENTION

More particularly according to the present invention, the electron donor group D is advantageously a radical selected from among the following:

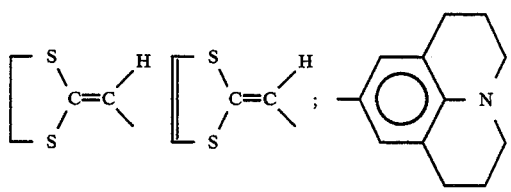

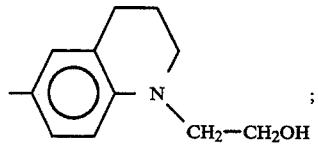

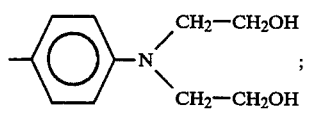

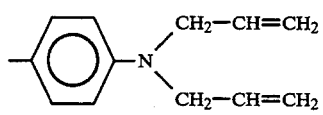

In another embodiment of the invention, the group D has the following general formula:

$-R_6-D_1$ in which $R_6$ is an aryl radical, preferably benzylidene radical, and $D_1$ is an electron donating radical selected from among amino, alkylamino, dialkylamino, arylamino, hydroxyl, thiolo, alkylthio, arylthio, alkoxy, aryloxy, halogenoalkyl, oxy,

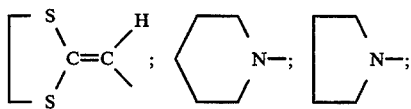

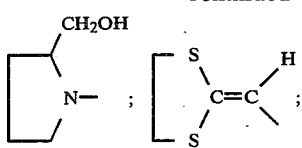

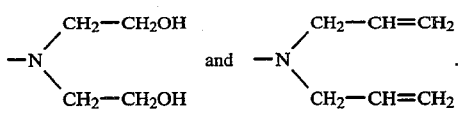

The preferred radical D of the invention is:

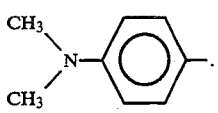

The A and $A_1$ groups, which may be identical or different, are advantageously hydrogen atoms or an electron acceptor radical selected from among nitro, cyano, —$CO_2R_5$ and —$PO_3(R_5)_2$ radicals, wherein $R_5$ is a lower alkyl radical, preferably ethyl or propyl.

Furthermore, the A and $A_1$ groups cannot simultaneously be hydrogen atoms.

The preferred radicals of the invention are the cyano and nitro radicals and, more particularly, the cyano/cyano and cyano/nitro combinations.

In a preferred embodiment of the invention, the novel compounds have a trans- configuration.

Particularly representative compounds according to the present invention have the following formulae:

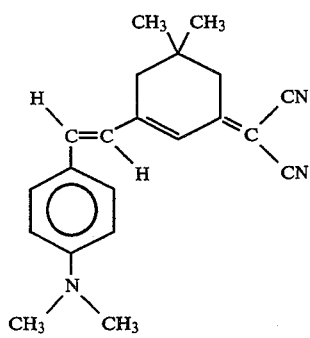

(A)

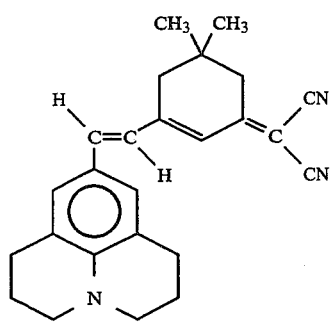

(B)

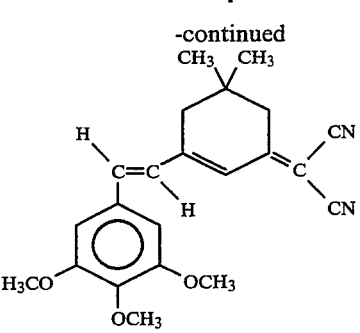

(C)

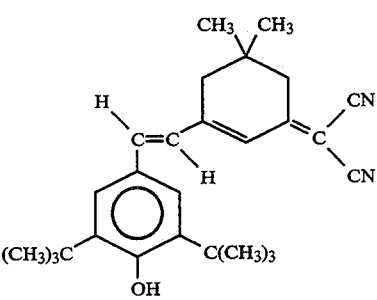

(D)

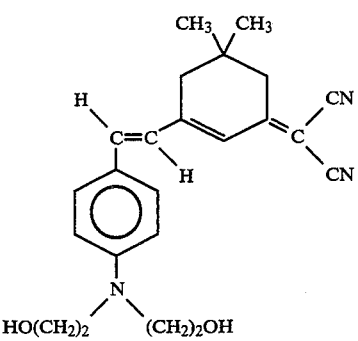

(E)

These compounds may be prepared by a number of different syntheses. Exemplary of such processes are those described in DE-2,345,189, in the article by Ralf Lemke, "Knoevenagel-Kondensationen in Dimethylformamid" (Knoevenagel condensations in dimethylformamide), published in *Synthesis*, 5, 359 (1974), or the article "Solvatochromie von 80 μm in verschiedmen Alkoholen bei Arylidenisophorm - Abkömmlignen", by the same author, published in *Chem. Ber.*, 103, 1894 (1970).

Briefly, such process entails carrying out the following reaction sequences:

-continued

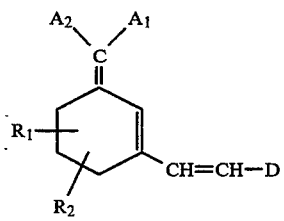

The latter condensation is known as the "Knoevenagel condensation".

The compounds of the invention display the important property of being optically active in nonlinear manner and, thus, well suited for incorporation in electronic or purely optical devices, in particular in the field of transducers, modulators, amplifiers, and the like.

In effect, the nonlinear optical activity is determined by the value of the coefficients $\beta$ and $\gamma$ of hyperpolarizability of the second, third or n order.

The hyperpolarizability of a compound is directly related to the dipolar molecular moment by the following fundamental relationship:

$$\mu = \mu o + \alpha \cdot E + \beta E \cdot E + \gamma E \cdot E \cdot E + \ldots$$

wherein $\mu$ and $\mu o$ represent the dipolar moments, respectively, in the presence and absence of an electromagnetic field.

E represents the electrical or local electromagnetic excitation field.

$\alpha$, $\beta$ and $\gamma$ represent the polarizability and hyperpolarizability coefficients.

Indeed, the $\alpha$ coefficient is the polarizability coefficient of the molecule and reflects its linear optical activity.

The $\beta$ and $\gamma$ coefficients represent the hyperpolarizability coefficients, respectively, of the second and third order.

These coefficients reflect the anharmonicity of the electric potential in the molecule and are strongly dependent on its symmetry and structure.

Furthermore, the coefficients of an odd order, such as the coefficient $\gamma$, are never zero for any molecule. In contrast, coefficients of an even order, such as the $\beta$ coefficient, are zero for centrosymmetrical molecules.

It is advantageous to use molecules having a nonzero coefficient for nonlinear optical applications, such as, for example, electrooptical devices, electrooptical modulators, parametric amplifiers, frequency doubling devices.

To appreciate and measure the $\beta$ coefficient of the molecules, it is determined by comparison with that of a reference molecule, i.e., urea.

The molecular hyperpolarizability $\beta$ of a compound may generally be determined by an experiment for generating the second harmonic. It is carried out in a solvent medium such as, for example, acetone, water or dimethylsulfoxide. The method designated EFISH, is applicable and is described in the articles by B. S. Levine et al, *Appl. Phys. Lett.*, Vol. 24, p. 445 (1974) and J. L. Houdar et al, *J. Chem. Phys.*, Vol. 67, p. 1,926 (1977).

It is also possible to measure the product $\mu\beta$ ($-w; w, O$) by determining the electrooptical capability $\chi^{(2)}$ ($-w; w, O$) of doped and polarized PMMA film containing N active molecules per unit volume. $\chi^{(2)}$ ($-w; w, O$) may be measured by interferometry as described in the article by K. D. Singer et al, *J. Opt. Soc. Am.*, B, Vol. 4, No. 6, p. 968 et seq (1987). The relationship between $\mu\beta$ and $\chi^{(2)}$ is well known; it is described, for example, in the article by K. D. Singer et al, *Appl. Phys. Lett.*, Vol. 49, No. 5, p. 248 et seq (1986).

The hyperpolarizability of the molecule may also be determined by a static $\beta\mu$ coefficient, which corresponds to the activity of the molecule at zero frequency and which thus yields a measure of the intrinsic activity of the molecule.

For this, $\beta\mu$ is measured at a given frequency, for example by one of the aforementioned methods, and the value obtained reduced to a hypothetical zero frequency by means of a calculation designated the "two level model".

The method of calculating the static $\beta\mu$ is described in the article by K. D. Singer, published in *J. Opt. Soc. Am.*, B/Vol. 4, No. 6, p. 968 et seq (1987).

In order to further illustrate the present invention and the advantages thereof, the following specific examples are given, it being understood that same are intended only as illustrative and in nowise limitative.

EXAMPLE 1

Preparation of the Compound (A)

Into a flask, 10 ml piperidine and 600 ml ethanol were introduced as solvents, followed by 0.268 mole of 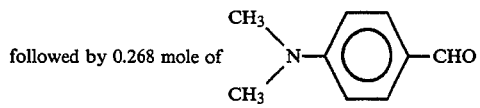

and 0.268 mole of 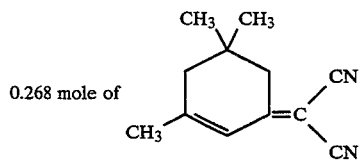

The mixture was maintained at reflux for 5 hours and then cooled to ambient temperature.

Compound (A) was recovered by filtration and washing with hexane.

The product collected was a red-violet solid having a melting point of 227° C.

NMR and mass spectrometry analyses confirmed the structure of Compound (A).

In addition, UV spectrometry analysis in a chloroform medium evidenced that the maximum wavelength ($\lambda$) of adsorption was 504 nm.

EXAMPLE 2

Preparation of the Compound (B)

To 100 ml ethanol, 0.268 mole of 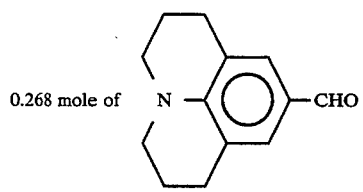

and 0.268 mole of 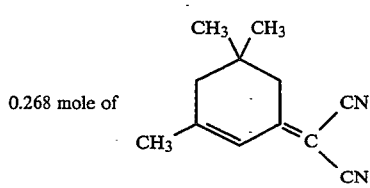

were added.

The mixture was heated to reflux for 48 hours and Compound (B) was permitted to crystallize at ambient temperature.

After filtration and washing with hexane, Compound (B) was recovered in the form of a violet solid with a melting point of 229° C.

NMR analysis, infrared and mass spectrography confirmed the structure of Compound (B).

The compound displayed, by UV spectrometry in a chloroform medium, a maximum adsorption wavelength of 550 nm.

EXAMPLE 3

Preparation of the Compound (C)

Following the procedure of Example 1, the compounds

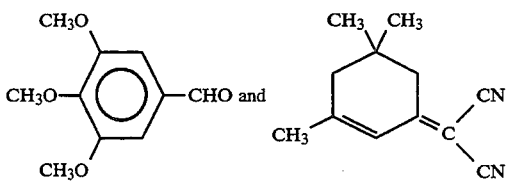

were reacted with each other.

Following crystallization, filtering and washing with hexane, an orange solid was recovered; it had a melting point of 211.5° C.

NMR analysis, IR and mass spectrometry confirmed the structure of Compound (C).

The maximum adsorption wavelength (λ max) under UV spectrometry was 420 nm (CHCl$_3$).

EXAMPLE 4

Preparation of the Compound (D)

Following the procedure of Example 2, the following compounds were reacted with each other:

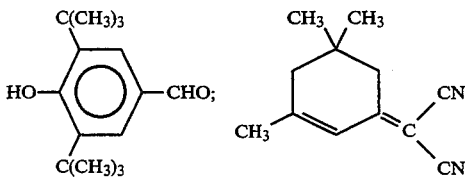

Following crystallization, filtering and washing with hexane, then recrystallization in a methanol/acetone mixture, a yellow-orange colored solid was recovered, having a melting point equal to 226.5° C. and λ max of 437 nm (CHCl$_3$).

In a manner similar to the preceding examples, the various analyses confirmed the structure of the Compound (D).

EXAMPLE 5

Preparation of the Compound (E)

This compound was prepared by the reaction of the following compounds with each other:

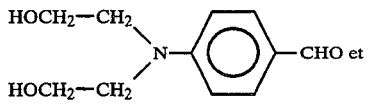

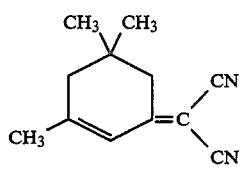

according to the procedure of Example 2.

The solvent was then evaporated to recover a red oil. Compound (E) was recovered by separation on a chromatographic column based on silica gel, with ethyl acetate as the eluant.

The product recovered was a red-violet solid having a melting point equal to 168° C. and having a λ max of 494 nm (CHCl$_3$).

As in the preceding examples, the various analyses confirmed the structure of Compound (E) as shown above.

The results of the determination of the hyperpolarizability coefficient and the static coefficient of the different compounds are reported in the following table:

TABLE

| Example | Compound | Hyperpolarizability Coefficient $\beta\mu$ ($-w$; w; O) at $\lambda = 633$ nm | Static Coefficient $\beta\mu \times 10^{-48}$ e.s.u. |
|---|---|---|---|
| 1 | A | 11,710 × 10$^{-48}$ esu | 2,170 |
| 2 | B | 7,390 × 10$^{-48}$ esu | 750 |
| 3 | C | 880 × 10$^{-48}$ esu | 330 |
| 4 | D | 2,050 × 10$^{-48}$ esu | 710 |
| 5 | E | 10,610 × 10$^{-48}$ esu | 1,780 |

The compounds of the invention are incorporated in components of electrooptical devices in the form of materials, such as, for example, in the form of a film, by formulating same in a matrix, such as a polymer, a resin, etc., by conventional and known techniques.

Thus, for example, the compounds prepared according to Examples 1 to 5, were incorporated in a transparent polymer film of a thickness of 0.5 to 200 μm, as described in EP-218,938. Exemplary such polymers are, for example, polymethylmethacrylate and atactic polystyrene.

The polymer film was heated to a temperature higher than its glass transition temperature (Tg), then subjected to an intense electrical field to orient the active molecules according to the invention.

The film was then cooled to a temperature less than its glass transition temperature Tg, to freeze the active molecules in the oriented position.

A film containing the active oriented molecules of the invention had an electrooptical coefficient and a coefficient of generation of the second order harmonic comparable to those of the crystals customarily used for such applications, such as, for example, potassium diphthalate, ammonium diphthalate, potassium dihydrogenophthalate.

The film also provided specific advantages, such as a low dielectric constant and an electrooptical activity essentially of electronic origin.

The optoelectronically active materials, in particular in the form of films, are suitable for use in electrooptical modulators, active guides, such as directional couplers, polarizers, integrated modulators, and the like.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A nonlinearly optically active compound having the formula

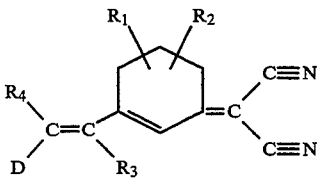

wherein the radical D has the general formula:

in which $R_6$ is an aryl radical, and $D_1$ is an electron donating radical selected from among amino, alkylamino, arylamino, thiol, alkylthio, alkoxy, aryloxy, halogenoalkyl, or one of the radicals

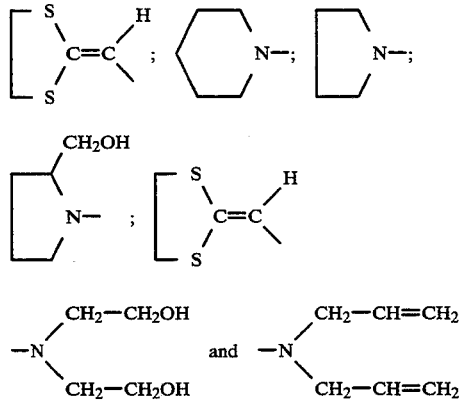

and $R_1$, $R_2$, $R_3$ and $R_4$ are each hydrogen or a lower alkyl radical.

2. The compound as defined in claim 1, wherein $R_6$ is a phenylene radical.

3. The compound as defined in claim 1, wherein $D_1$ is a thiol radical.

4. The compound as defined in claim 1, wherein $D_1$ is an alkylthiol radical.

5. The compound as defined in claim 1, wherein $D_1$ is an alkoxy radical.

6. The compound as defined in claim 1, wherein $D_1$ is an aryloxy radical.

7. The compound as defined in claim 1, wherein $D_1$ has one of the formulae:

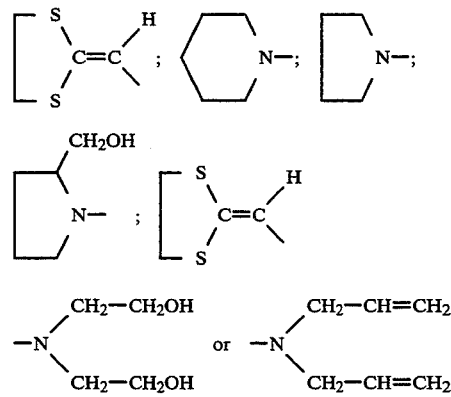

8. A nonlinearly optically active compound having one of the following structural formulae:

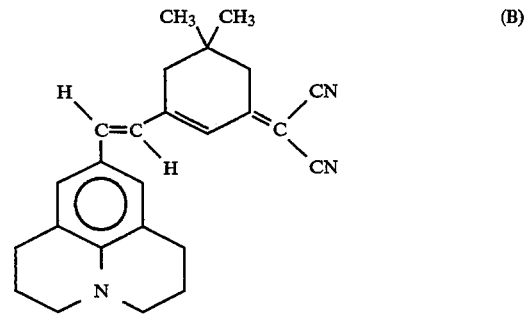

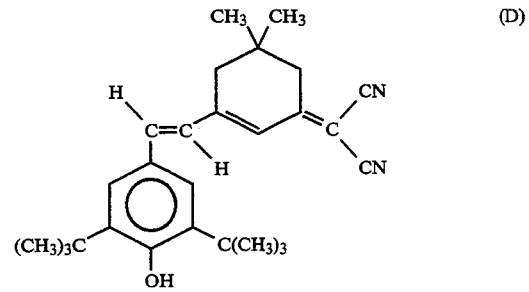

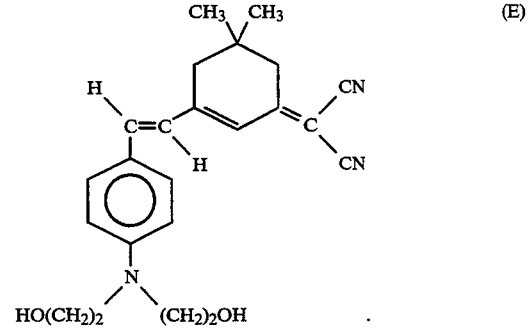

9. The nonlinearly optically active compound as defined by claim 8, wherein said compound has the formula (B).

10. The nonlinearly optically active compound as defined by claim 8, wherein said compound has the formula (D).

11. The nonlinearly optically active compound as defined by claim 8, wherein said compound has the formula (E).

* * * * *